(12) United States Patent
Hallahan

(10) Patent No.: US 7,232,844 B2
(45) Date of Patent: *Jun. 19, 2007

(54) INSECT REPELLENT COMPOUNDS

(75) Inventor: David L. Hallahan, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/964,415

(22) Filed: Oct. 13, 2004

(65) Prior Publication Data

US 2005/0069568 A1 Mar. 31, 2005

Related U.S. Application Data

(62) Division of application No. 10/392,455, filed on Mar. 19, 2003, now abandoned.

(60) Provisional application No. 60/366,147, filed on Mar. 20, 2002.

(51) Int. Cl.
*A61K 31/352* (2006.01)
*C07D 311/94* (2006.01)

(52) U.S. Cl. ..................... 514/456; 549/283

(58) Field of Classification Search ................ 514/456; 549/283
See application file for complete search history.

(56) References Cited

U.S. PATENT DOCUMENTS

| | | | |
|---|---|---|---|
| 4,663,346 | A | 5/1987 | Coulston et al. |
| 4,869,896 | A | 9/1989 | Coulston et al. |
| 5,753,686 | A | 5/1998 | Marin et al. |
| 6,462,015 | B1 | 10/2002 | Weiss et al. |
| 6,524,605 | B1 | 2/2003 | Coats et al. |
| 2003/0073748 | A1 | 4/2003 | Henderson et al. |
| 2003/0191047 | A1 | 10/2003 | Hallan |
| 2004/0024054 | A1 | 2/2004 | Haenke |

FOREIGN PATENT DOCUMENTS

| EP | 0 167 265 | 1/1986 |
|---|---|---|
| EP | 0 450 087 A1 | 4/1991 |
| EP | 0 450 087 | 10/1991 |
| WO | WO 03/086069 | 10/2003 |

OTHER PUBLICATIONS

C. E. Schreck, D. Fish and T. P. McGovern, Activity of Repellents Applied to Skin for Protection against Amblyomma a Americanum and Ixodes Scapularis Ticks (Acari: Ixodidae), Journal of the American Mosquito Association, 11(1) 136-140, 1995.
R. K. M. Hay, and K. P. Svoboda, Botany Volatile Oil Crops, Their Biology and Production, p. 5-22, 1993.
L. J. Clark, J. G. C. Hamilton, June V. Chapman, Michael J. C. Rhodes and David L. Hallahan, Analysis of monoterpenoids in glandular trichomes of the catmint Nepeta racemosa. The Plant Journal (1997) 11(6). 1387-1393.
G. Briassoulis, M. Narlioglou and T. Hatzis, Toxic encephalopathy associated with use of DEET insect repellents: a case analysis of its toxicity in children, Human & Experimental Toxicology (2001) 20, 8-14.
Chris Peterson and Joel Coats, Insect Repellents—Past, Present and Future, Pesticide Outlook, Aug. 2001.
Peterson, C. et al. (2001) Abstracts of Papers American Chemical Society 222 (1-2).
Eisner, T. (1965) Science, vol. 148, pp. 966-968.
Eisner, T. (1964) Science, vol. 146, pp. 1318-1320.
Hollon, T., For Tomorrow's Infantry: SS-220, a Gunsight-Friendly Insect Repellent, The Scientist, Jun. 16, 2003, pp. 25-26.
Inouye, H., Iridoids, Methods in Plant Biochemistry, vol. 7 pp. 99-143, 1991.
New Scientist, "The Sweet Smell of Death", pp. 28-31, Sep. 7, 1996.
Pesticide Outlook, "Pesticides Based on Plant Essential Oils", pp. 68-72, Apr. 1999.
Brattsten, Lena B, "Cytochrome P-450 Involvement in the Interactions Between Plant Terpenes and Insect Herbivores", pp. 173-195, 1983, Knoxville, TN.
Abstract of Braverman, Y, Mosquito repellent attracts Culicoides imicola (Diptera: Ceratopogonidae), Journal of Medical Entomology, Jan. 1999, pp. 113-115, vol. 36, No. 1.
Abstract of Krell, Frank-Thorsten, et al., "Dung bettles attracted by a commercial insect repellent", Entomologists' Monthly Magazine, Apr.-Jun. 2003, pp. 91-96, vol. 139, No. 1667-1669.
Barasa, et al., Repellent Activities of Stereoisomers of p-Menthane-3,8-diols Against Anopheles gambiae (Diptera: Culicidae). (2002) J. Med. Entomol, vol. 39, Issue 5, pp. 736-741.
Bergmann, et al., "Study of Synthetic Compounds as Repellents Against the Mosquitoes Culex Pipiens Molestus and Aedes Aegypti", Israel Journal of Entomollgy, (1976) vol. XI, pp. 15-61.
Dawson, et al., "The aphid sex pheromone", Pure & Appl. Chem., (1989), vol. 61, No. 3, pp. 555-558.
R. Lilley, et al., "The Aphid Sex Pheromone: A Novel Host Location Cue for the Parasitoid Praon Volucre", Brighton Crop Protection Conference—Pests and Disease, (1994), pp. 1157-1162.
W.A. Skinner, el al., "The Design of Insect Repellents", Drug Design, (1980), vol. X, pp. 278-305.
C.J. Peterson, et al., ":Catnip Essential Oil as a Barrier to Subterranean Termites (Isoptera: Rhinotermitidae) in the Laboratory", Household and Structural Insects, J. Econ. Entomol., 1996, pp. 1275-1282) vol. (4), Starkville, MS.

(Continued)

*Primary Examiner*—Taofiq Solola

(57) ABSTRACT

Dihydronepetalactone, a minor natural constituent of the essential oil of catmints (*Nepeta* spp.) such as *Nepeta cataria*, has been identified as an effective insect repellent compound. Synthesis of dihydronepetalactone may be achieved by hydrogenation of nepetalactone, the major constituent of catmint essential oils. This compound, which also has fragrance properties, may be used commercially for its insect repellent properties.

30 Claims, 7 Drawing Sheets

OTHER PUBLICATIONS

Database CAPLUS on STN, Dep. Chemistry, Cornell Univ., (Ithaca, NY), No. 1983: 104758, Jefson, M. et al., "Chemical defense of a rove bettle (*Creophilus maxillosus*)", abstract, Journal of Chemical Ecology. 1983, Vo. 9, No. 1, pp. 159-180, 1983.

Jefson, et al., "Chemical Defense of a Rove Beetle", Journal of Chemical Ecology, (1983) pp. 159-180, vol. 9, No. 1, Ithaca, New York.

G.W.K. Cavill, "Defensive and Other Secretions of the Australian Cocktail Ant, Iridomyrmex Nitidiceps", Tetrahedron, (1982), pp. 1931-1938. vol. 38, No. 13, Great Britian.

G.W.K. Cavill, et al., "Insect Venoms, Attractants, and Repellents—VIII, Isohihydronepetalactone", J. Insect Physiol, (1967), pp. 131-135, vol. 13, Great Britain.

Abelman, et al., "Alicyclic Claisen Rearrangement. A General Carbocycle Synthesis Based on Four-Atom-Ring Contractions of Lactones", J.Am. Chem. Soc., (1982) pp. 4030-4032, vol. 104, Lincoln, Nebraska.

Fleming, et al., "Stereospecific Allylisilane Reactions: A Total Synthesis of Dihydronepetalactone", Tetrahedron Letters, (1984) vol. 25, No. 44. pp. 5103-5104, vol. 44, Cambridge, England.

Fleming, et al., "Stereocontrol in organic synthesis using silicon-containing compounds. A synthesis of (+)- dihydronepetalactone using the $S_E2'$ reaction of an allylsilane", J.Chem. Soc., Perkin Trans (1998), vol. 1, pp. 2645-2649, Cambridge.

Nagata, et al., "Concurrent resolution and oxidation of an allylic acetate and its utilzation in the diastereocontrolled synthesis of some cyclopentanoid monterpenes", Tetrahedron Letters, (1999), vol. 40, pp. 6617-6620, Japan.

Nangia, et al., "Intramolecular Horner-Wadswroth-Emmons Reaction in Base Sensitive Substrates: Enantiospecific Synthesis of Iridold Monoterpene Lactones", Tetrahedron Letters, (1994), vol. 35, No. 22, pp. 3755-3758, India.

Uyehara, et al., "New Type of Cyclization of a,B,X, ↓-Unsaturated Dioic Acid Esters through Tandem Conjugates Additions by Using Lithium N-Benzyl-N-(trimethylsilyl) amide as a Nitrogen Nucleophile", J. Org. Chem., (1992), vol. 57, No. 11, pp. 3139-3145, Japan.

Wolinsky, et al., "Syntheses of the Dihydronepetalactones", J. Org. Chem., (1972), vol. 37, No. 21, pp. 3376-3378, Indiana.

Wolinsky, et al., "The Synthesis of (+) Matatabiether and Related Methylcyclopentane Monoterpenes", Tetrahedron, (1969), vol. 25, pp. 3767 to 3774, Great Britain.

Uyehara, et al., Cyclisation of a,B,x,u-Unsaturated Dioic Acid Esters via Tendem Conjugate Additions by using Lithium N-Benzyltrimethylsilylamide (LSA) as a Nitrogen Nucleophile and its (+)-Isodihydronepetalactone., (1989) J. Chem. Soc., Chem. Commun., pp. 113-114, Japan.

Lee, et al., "Stereoselective Favorskii Rearrangement of Carvone Chlorohydrin; Expedient Synthesis of (+)- Dihydronepetalactone and (+)-Iridomyrmecin", J.Chem., Soc., Chem. Commun., (1994), pp. 479-481, Korea.

Tanimori, et al., "Total Synthesis of (+)-Dihydronepetalactone", Agric. Biol. Chem., (1991), pp. 1181-11832, vol. 55, No. 4, Japan.

Ramanathan Natarajan et al., Chirality Index, Molecular Overlay and Biological Activity of Diastereoisomeric Mosquito Repellents, Pest Management Science, vol. 61:1193-1201, 2005.

Arthur O. Tucker et al., Catnip and the Catnip Response, Economic Botany, vol. 42:214-231, 1988.

(4aS,7S,7aR) nepetalactone
(cis,trans-nepetalactone)

(4aR,7S,7aS) nepetalactone
(cis,cis-nepetalactone)

(4aS,7S,7aS) nepetalactone
(trans,cis-nepetalactone)

(4aR,7S,7aR) nepetalactone
(trans,trans-nepetalactone)

INSECT REPELLENT COMPOUNDS

This application is a division of application Ser. No. 10/392,455, filed Mar. 19, 2003, now abandoned which is incorporated in its entirety as a part hereof for all purposes, and which claimed the benefit of U.S. Provisional Application No. 60/366,147, filed Mar. 20, 2002.

FIELD OF THE INVENTION

The present invention relates to the field of insect repellency, and the use of dihydronepetalactone stereoisomers generally as repellent materials.

BACKGROUND OF THE INVENTION

Repellent substances generally cause insects to be driven away from, or to reject, otherwise insect-acceptable food sources or habitats. Most known repellents are only mildly toxic. A few of the known repellents, in fact, are not active poisons at all but rather prevent damage to plants/animals or articles of manufacture by making insect food sources or living conditions unattractive or offensive. Most current commercial insect repellents contain the synthetic chemical N,N-diethyl-m-toluamide (DEET) as their primary active ingredient. For instance, repellents sold under the major commercial brand names such as Off!®, Deep Woods Off!®, and Cutter® are all DEET based products and comprise 85% of insect repellent sales (Consumer Reports Buying Guide, 1994 Special Year-End Issue). Further, Consumer Reports tests indicated that products with the highest concentration of DEET lasted the longest against mosquitoes. Despite being an effective repellent, however, this compound has certain drawbacks. Specifically, it possesses an unpleasant odor and imparts a greasy feel to the skin. Although it has recently been re-registered for use in the US by the EPA, concerns have been raised as to its safety, particularly when applied to children (Briassoulis, G.; Narlioglou, M.; Hatzis, T. (2001) *Human & Experimental Toxicology* 20(1), 8-14). Studies have demonstrated that high concentrations of DEET may give rise to allergic or toxic reactions in some individuals. Other disadvantages associated with DEET include: 1) it is a synthetic chemical having a limited spectrum of activity; 2) DEET is a powerful plasticizer and will dissolve or mar many plastics and painted surfaces; and 3) DEET plasticizes the inert ingredients typically used in topical formulations in order to lengthen the time of effectiveness. This leads to DEET formulations with low user acceptability.

As a result of the above limitations, DEET-free products with repellent activity are finding favor with consumers, and demand for compositions containing natural products (versus synthetic chemicals such as DEET) is increasing. These DEET-free repellent compounds require a combination of excellent repellency, high residual activity and relatively little or no toxicity to humans (or pets) and the environment. In response to these consumer demands, there is an on-going need to develop new repellent compounds which can be obtained from, or synthesized from, natural plant materials and which are pleasant to use.

Many plant species produce essential oils (aromatic oils) which are used as natural sources of insect repellent and fragrant chemicals [Hay, R. K. M., Svoboda, K. P., Botany, in 'Volatile Oil Crops: their biology, chemistry and production'. Hay, R. K. M., Waterman, P. G. (eds.). Longman Group UK Limited (1993)]. Citronella oil, known for its general repellence towards insects, is obtained from the graminaceous plants *Cymbopogon winterianus* and *C. nardus*. Examples of plants used as sources of fragrant chemicals include *Melissa officinalis* (Melissa), *Perilla frutescens* (Perilla), *Posostemon cablin* (Patchouli) and various *Lavandula* spp. (Lavender). All of these examples of plants yielding oil of value to the fragrance industry are members of the Labiatae (*Lamiaceae*) family. Plants of the genus *Nepeta* (catmints) are also members of this family, and produce an essential oil which is a minor item of commerce. This oil is very rich in a class of monoterpenoid compounds known as iridoids [Inouye, H. *Iridoids. Methods in Plant Biochemistry* 7:99-143 (1991)], more specifically the methylcyclopentanoid nepetalactones [Clark, L. J. et al. *The Plant Journal*, 11:1387-1393 (1997)] and derivatives.

Iridoid monoterpenoids have long been known to be effective repellents to a variety of insect species (Eisner, T. *Science* 146:1318-1320 (1964); Eisner, T. *Science* 148:966-968 (1965); Peterson, C. and J. Coats, *Pesticide Outlook* 12:154-158 (2001); and Peterson, C. et al. *Abstracts of Papers American Chemical Society*, (2001) 222 (1-2): AGRO73). U.S. Pat. No. 4,663,346 discloses insect repellants with compositions containing bicyclic iridoid lactones (e.g., iridomyrmecin). Further, U.S. Pat. No. 4,869,896 discloses use of these bicyclic iridoid lactone compositions in potentiated insect repellent mixtures with DEET.

Formal studies concerning the repellency of dihydronepetalactones, a class of iridoid monoterpenoids derived from nepetalactones (shown in FIG. 1), have been much less conclusive and have failed to teach or imply that these compounds exert a repellent effect on the common insect pests of human society. For example, a study of the composition of the secretion from anal glands of the ant *Iridomyrmex nitidus* showed that isodihydronepetalactone was present in appreciable amounts, together with isoiridomyrmecin (Cavill, G. W. K., and D. V. Clark. *J. Insect Physiol.* 13:131-135 (1967)). Although isoiridomyrmecin was known at the time to possess good 'knockdown' insecticidal activity, no evidence was provided in support of a similar activity for isodihydronepetalactone, and no investigation of this compound's repellent effect (as distinct from insecticidal activity) was made.

In a later publication by Cavill, G. W. K., et al. (*Tetrahedron* 38:1931-1938 (1982)), the presence of dihydronepetalactones in the defensive secretion of an ant was again reported, but the authors concluded that the compound iridodial (and not a dihydronepetalactone) was the basic repellent constituent.

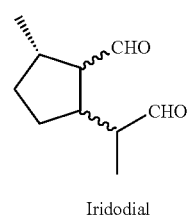

Iridodial

Most recently, Jefson, M., et al. (*J. Chemical Ecology* 9:159-180 (1983)) described the repellent effect of dihydronepetalactone. Initial repellency caused by the undiluted compound was measured with respect to the ant species *Monomorium destructor* during feeding. After 25 seconds of exposure to the pure dihydronepetalactone, approximately 50-60% of the ants ceased to feed. However, further analyses of the repellency over a longer time course were not presented, nor were analyses with anything other than the pure undiluted compound. Repellency observed over such short periods of time (seconds) with concentrated chemicals is insufficient to allow prediction of efficacy in practical applications such as in topical insect repellents.

There is consequently a continuing need for a biologically-based compound having improved insect repellent properties (with respect to DEET) and which is substantially non-toxic or only mildly toxic to humans. Preferred repellents will have activity against a wide variety of insects, including biting insects, wood-boring insects, noxious insects, household pests, and the like. Applicants have found that dihydronepetalactones perform well as a new class of effective insect repellent compounds without the disadvantageous properties characteristic of prior-art compositions.

SUMMARY OF THE INVENTION

One embodiment of this invention is an insect repellent composition or article that contains a dihydronepetalactone, or a mixture of dihydronepetalactone stereoisomers, represented by the general formula:

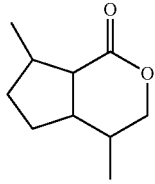

Another embodiment of this invention is a process for fabricating an insect repellent composition or an insect repellent article of manufacture by providing as the composition or article, or incorporating into the composition or article, a diihydronepetalactone, or a mixture of dihydronepetalactone stereoisomers, as described above. A further embodiment of this invention is a method of imparting, augmenting or enhancing the insect repellent effect of an article by incorporating into the article a diihydronepetalactone, or a mixture of dihydronepetalactone stereoisomers, as described above.

Yet another embodiment of this invention is the use of a diihydronepetalactone, or a mixture of dihydronepetalactone stereoisomers, as described above as an insect repellent, and thus in a method of repelling insects, the insects are exposed to a diihydronepetalactone, or a mixture of dihydronepetalactone stereoisomers, as described above.

DETAILED DESCRIPTION OF THE INVENTION

Figure 1:
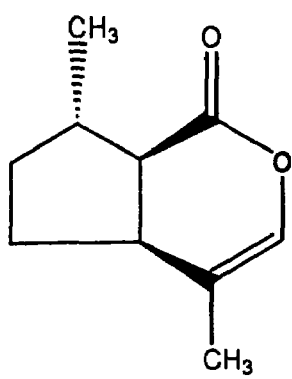
FIG. 1 shows the chemical structures of the naturally-occurring iridoid (methylcyclopentanoid) nepetalactones.
Figure 1:
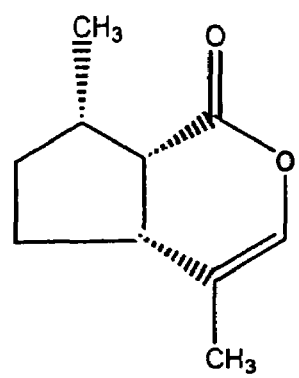
Figure 1:
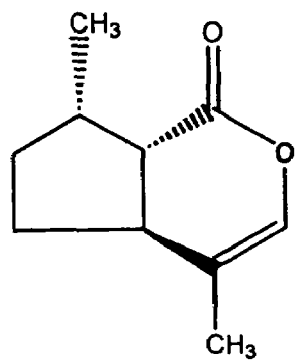
Figure 1:
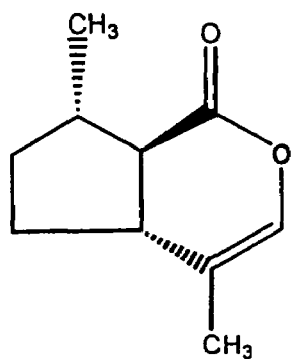

As used herein, the term "nepetalactone" refers to the compound having the general structure:

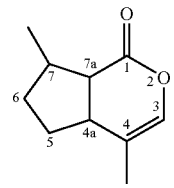

Four chiral centers are present within the methylcyclopentanoid backbone of nepetalactone at carbons 4, 4a, 7 and 7a as shown above; (7S)-nepetalactones are produced by several plants and insects. Dihydronepetalactones are defined by Formula 1:

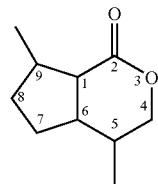

Formula 1 wherein 1, 5, 6 and 9 indicate the four chiral centers of the molecule and the structure encompasses all possible stereoisomers of dihydronepetalactone. The structures of dihydronepetalactone stereoisomers that may be derived from (7S)-nepetalactones are shown below.

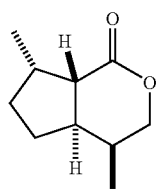

(1S, 5S, 9S, 6R)-5, 9-dimethyl-3-oxabicyclo[4.3.0]nonan-2-one

-continued

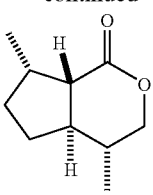

(1S, 9S, 5R, 6R)-5, 9-dimethyl-3-oxabicyclo[4.3.0]nonan-2-one

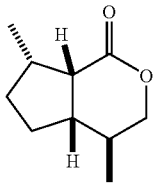

(1S, 5S, 9S, 6S)-5, 9-dimethyl-3-oxabicyclo[4.3.0]nonan-2-one

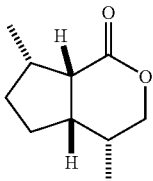

(1S, 9S, 6S, 5R)-5, 9-dimethyl-3-oxabicyclo[4.3.0]nonan-2-one

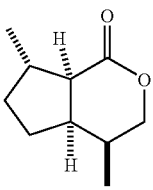

(9S, 5S, 1R, 6R)-5, 9-dimethyl-3-oxabicyclo[4.3.0]nonan-2-one

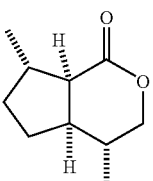

(9S, 1R, 5R, 6R)-5, 9-dimethyl-3-oxabicyclo[4.3.0]nonan-2-one

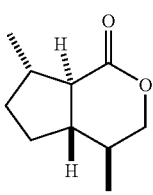

(9S, 6S, 1R, 5S)-5, 9-dimethyl-3-oxabicyclo[4.3.0]nonan-2-one

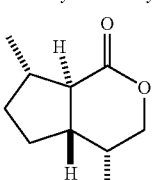

(9S, 6S, 1R, 5R)-5, 9-dimethyl-3-oxabicyclo[4.3.0]nonan-2-one

As used herein, the term "dihydronepetalactones" or "dihydronepetalactone mixtures" refers to any mixture of dihydronepetalactone stereoisomers. The molar or mass composition of each of these isomers relative to the whole dihydronepetalactone composition can be variable. Dihydronepetalactones are abbreviated as "DHN".

As used herein, the term "insect" refers to any member of a large group of invertebrate animals characterized, in the adult state (non-adult insect states include larva and pupa) by division of the body into head, thorax, and abdomen, three pairs of legs, and, often (but not always) two pairs of membranous wings. This definition therefore includes a variety of biting insects (e.g., ants, bees, black flies, chiggers, fleas, green head flies, mosquitoes, stable flies, ticks, wasps), wood-boring insects (e.g., termites), noxious insects (e.g., houseflies, cockroaches, lice, roaches, wood lice), and household pests (e.g., flour and bean beetles, dust mites, moths, silverfish, weevils).

As used herein, the term "host" hereinafter refers to any plant or animal affected by insects. Typically, hosts are considered to be insect-acceptable food sources or insect-acceptable habitats.

As used herein, the term "insect susceptible article" will refer to any item of commerce created by man, which is affected by insects. This may include buildings, furniture, and the like. Typically, these articles of manufacture are considered to be insect-acceptable food sources or insect-acceptable habitats.

As used herein, the term "insect repellent" or "insect repellent composition" or "repellent composition" will refer to a compound or composition which deters insects from their preferred hosts or insect-suitable articles of manufacture. Most known repellents are not active poisons at all, but rather prevent damage to plants/animals or articles of manufacture by making insect food sources or living conditions unattractive or offensive. Typically, insect repellents are a compound or composition that can be either topically applied to the host; or, the compound or composition is incorporated into an insect susceptible article to produce an insect repellent article that deters insects from the nearby 3-dimensional space in which the host or article exists. In either case, the affect of the insect repellent is to drive the insects away from or to reject: 1.) the host, thereby minimizing the frequency of insect "bites" to the host; or 2.) the insect susceptible article, thereby protecting the article from insect damage. Repellents may be in the form of gases (olfactory), liquids, or solids (gustatory).

Some examples of well-known insect repellents include: benzil; benzyl benzoate; 2,3,4,5-bis(butyl-2-ene)tetrahydrofurfural(MGK Repellent 11); butoxypolypropylene glycol; N-butylacetanilide; normal-butyl-6,6-dimethyl-5,6-dihydro-1,4-pyrone-2-carboxylate (Indalone); dibutyl adipate; dibutyl phthalate; di-normal-butyl succinate (Tabatrex); N,N-diethyl-meta-toluamide (DEET); dimethyl carbate (endo, endo)-dimethyl bicyclo[2.2.1]hept-5-ene-2,3-dicarboxylate); dimethyl phthalate; 2-ethyl-2-butyl-1,3-propanediol; 2-ethyl-1,3-hexanediol (Rutgers 612); di-normal-propyl isocinchomeronate (MGK Repellent 326); 2-phenylcyclohexanol; p-methane-3,8-diol, and normal-propyl N,N-diethylsuccinamate. Standard repellents for mosquitoes, ticks, and the like are citronella oil (discussed below), dimethyl phthalate, normal-butylmesityl oxide oxalate and 2-ethyl hexanediol-1,3 (See, Kirk-Othmer Encyclopedia of Chemical Technology, $2^{nd}$ Ed., Vol. 11: 724-728; and The Condensed Chemical Dictionary, $8^{th}$ Ed., p 756).

In addition to the chemical compositions above, a variety of effective insect repellents consist of essential oils and/or active ingredients of essential oils. "Essential oils" are defined as any class of volatile oils obtained from plants possessing the odor and other characteristic properties of the plant. Examples of repellent compounds that are essential oils include: almond bitter oil, anise oil, basil oil, bay oil, caraway oil, cardamom oil, cedar oil, celery oil, chamomile oil, cinnamon oil, citronella oil, clove oil, coriander oil, cumin oil, dill oil, eucalyptus oil, fennel oil, ginger oil, grapefruit oil, lemon oil, lime oil, mint oil, parsley oil, peppermint oil, pepper oil, rose oil, spearmint oil (menthol), sweet orange oil, thyme oil, turmeric oil, and oil of wintergreen. Examples of active ingredients in essential oils are: citronellal, methyl salicylate, ethyl salicylate, propyl salicylate, citronellol, safrole, and limonene.

In contrast to an "insect repellent", an "insecticide" is a compound or mixture which is capable of poisoning an insect via its oral ingestion, by contact with the insect cuticle, or by fumigant action through the air. Thus, an insecticide is a type of pesticide designed to control insect life which is harmful to man (i.e., directly harmful as disease vectors, or indirectly harmful by destruction of crops, food products, or textile fabrics). Several well-known insecticides include: inorganic compounds (such as arsenic, lead and copper); naturally occurring organic compounds (such as rotenone, pyrethrins, nicotine, copper naphthenate and petroleum derivatives); and synthetic organic compounds (such as DDT, dieldrin, endrin, chlordane, lindane, paradichlorobenzene and parathion).

As used herein, the term "potentiated insect repellent composition" refers to a repellent composition which produces a result substantially in excess of that which reasonably could be expected or predicted from the known effect of the components either alone or additively. In the present invention, a potentiated insect repellent composition will include dihydronepetalactones or a mixture thereof, and at least one other insect repellent compound that is not itself dihydronepetalactone (sometimes referred to as a non-dihydronepetalactone insect repellent compound).

An "insect repellent composition" can be used as a component of an "insect repellent article", wherein the term "insect repellent article" refers to an article of manufacture possessing insect repellency that is enhanced, altered, or augmented by the insect repellent composition. As used herein with respect to insect repellency, the terms "alter" and "modify" in their various forms refer to a means of supplying or imparting insect repellency to a composition, or augmenting the existing insect repellency characteristics where natural repellency is deficient in some regard, or supplementing the existing insect repellency to modify its quality, or character. The term "enhance" is intended to mean the intensification (without effecting a change in kind or quality of repellency) of one or more repellency properties in an insect repellent composition or insect repellent article.

In a preferred embodiment, the insect repellent composition of this invention also functions as a fragrance composition since it is capable of imparting a pleasing fragrance or aroma to the insect repellent composition or to an insect repellent article. Dihydronepetalactones are useful in an insect repellent composition or article to enhance, alter, or augment the overall aroma or fragrance of the composition or article. With respect to fragrance, the terms "alter" and "modify" in their various forms refer to a means of supplying or imparting a fragrance or aroma character or note to otherwise bland substances or augmenting the existing aroma characteristics where natural aroma is deficient in some regard or supplementing the existing aroma impression to modify its quality, character, or aroma. The term "enhance" is intended to mean the intensification (without effecting a change in kind or quality of aroma) of one or more aroma nuances and their organoleptic impression of a fragrance, perfume composition, or one or more perfumed articles.

The term "fragrance composition" is used herein to mean a mixture of organic compounds including, for example, alcohols, aldehydes, ketones, nitriles, esters, lactones, natural essential oils, synthetic essential oils, and mercaptans, which are admixed so that the combined odors of the individual components produce a pleasant or desired fragrance. Such compositions usually contain: (1) the main note or the "bouquet" or foundation stone of the composition; (2) modifiers which round off and accompany the main note; (3) fixatives which include odorous substances which lend a particular note to the perfume throughout all stages of evaporation and substances which retard evaporation; and (4) top notes which are usually low-boiling, fresh-smelling materials.

In fragrance or aroma compositions, the individual component will contribute its particular olfactory characteristics, but the overall effect of the composition will be the sum of each of the effects of each of the ingredients. Thus, the dihydronepetalactones of this invention or mixtures thereof can be used to alter the aroma characteristics of such compositions, for example, by highlighting or moderating the olfactory reaction contributed by another ingredient in the composition.

Dihydronepetalactones are known in the literature, for example as minor constituents of the essential oils of several labiate plants of the genus *Nepeta* (Regnier, F. E., et al. *Phytochemistry* 6:1281-1289 (1967); DePooter, H. L., et al. *Flavour and Fragrance Journal* 3:155-159 (1988); Handjieva, N. V. and S. S. Popov *J. Essential Oil Res.* 8:639-643 (1996)). Additionally, dihydronepetalactones have been identified as constituents of the defensive secretions of certain insects, including rove beetles (Jefson, M., et al. *J. Chem. Ecol.* 9:159-180 (1983)) and ants, specifically *Iridomyrmex* species (Cavill, G. W. K. and D. V. Clark. *J. Insect Physiol.* 13:131-135 (1967)). In those species that possess dihydronepetalactones, it has been proposed that they are biosynthetically derived from the iridoid monoterpene iridodial.

The chemical synthesis of dihydronepetalactones and their related iridoid monoterpenoid compounds has been described and found to be conducted in a variety of ways. The following are useful references relating to synthesis:

1) Abelman, M. M. et al. *J. Am. Chem. Soc.* 104(14): 4030-2 (1982)

2) Fleming, I. and N. K. Terrett. *Tetrahedron Lett.* 25(44): 5103-5104 (1984); *J. Chem. Soc., Perkin Trans.* 1:2645-2650 (1998).

3) Lee, E. and C. H. Yoon. *J. Chem. Soc., Chem. Commun.* 4: 479-81 (1994).

4) Nagata, H. and K. Ogasawara. *Tetrahedron Lett.* 40(36): 6617-6620 (1999).

5) Nangia, A. et al. *Tetrahedron Lett.* 35(22): 3755-8 (1994).

6) Tanimori, S. and M. Nakayama. *Agric. Biol. Chem.* 55(4): 1181-1184 (1991).

7) Uyehara, T. et al. *J. Chem. Soc., Chem. Commun.* 2:113-14 (1989); *Tennen Yuki Kagobutsu Toronkai Koen Yoshishu* 32: 441-6 (1990); *J. Org. Chem.* 57(11): 3139-3145 (1992).

8) Wolinsky, J. and E. J. Eustace. *J. Org. Chem.* 37(21): 3376-8 (1972).

9) Wolinsky, J. and D. L. Nelson. *Tetrahedron* 25(17): 3767-74 (1969).

One preferred and convenient method for synthesis of the dihydronepetalactone mixtures of the present invention is by hydrogenation of nepetalactone. Catalysts such as platinum oxide and palladium supported on strontium carbonate give dihydronepalactone in 24-90% yields (Regnier, F. E., et al. *Phytochemistry* 6:1281-1289 (1967)). Nepetalactone is a known material that can be conveniently obtained in relatively pure form from the essential oils isolated by various means from plants of the genus *Nepeta* (catmints). Isolation of such oils is well known in the art, and examples of methodology for oil extraction include (but are not limited to) steam distillation, organic solvent extraction, microwave-assisted organic solvent extraction, supercritical fluid extraction, mechanical extraction and enfleurage (initial cold extraction into fats followed by organic solvent extraction).

The essential oils isolated from different *Nepeta* species are well known to possess different proportions of each naturally-occurring stereoisomer of nepetalactone (Regnier, F. E., et al. *Phytochemistry* 6:1281-1289 (1967); DePooter, H. L., et al. *Flavour and Fragrance Journal* 3:155-159 (1988); Handjieva, N. V. and S. S. Popov. *J. Essential Oil Res.* 8:639-643 (1996)). Thus, from oil derived from any *Nepeta* species containing a mixture of nepetalactones, a mixture of dihydronepetalactone stereoisomers will be generated upon hydrogenation. Four chiral centers are present within the methylcyclopentanoid backbone of the nepetalactone at carbons 4, 4a, 7 and 7a as shown:

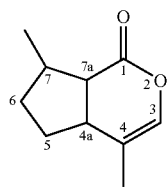

Thus it is clear that a total of eight pairs of dihydronepetalactone enantiomers are possible after hydrogenation. Of these, the naturally occurring stereoisomers described thus far are (9S)-dihydronepetalactones. Preferred repellent materials in accordance with the present invention include a mixture of any or all of the possible stereoisomers of dihydronepetalactone. More preferred repellent materials include a mixture of (9S)-dihydronepetalactones. Most preferred are (9S)-dihydronepetalactone stereoisomers derived from (7S)-nepetalactones. This includes the compounds commonly known as cis,trans-nepetalactone, cis,cis-nepetalactone, trans,cis-nepetalactone, and trans,trans-nepetalactone, as illustrated in FIG. 1.

Upon completion of the hydrogenation reaction, the resulting mixture of isomer products may be separated by a conventional method (e.g., preparative liquid chromatography) to yield each highly purified pair of dihydronepetalactone diastereomers.

In addition to variation in nepetalactone stereoisomer content between different *Nepeta* species, intra-species variation is also known to exist. Plants of a given species may produce oils with different compositions depending on the conditions of their growth or growth stage at harvest. Additionally, within a single species, *Nepeta racemosa*, variation in oil composition independent of growth conditions or growth stage at harvest has been demonstrated (Clark, L. J., et al. *The Plant Journal*, 11:1387-1393 (1997)). Plants of a single species exhibiting different oil compositions are termed chemotypes, and it has been shown that in *Nepeta racemosa*, chemotypes exhibiting marked differences in the proportion of different nepetalactone stereoisomers exist (Clark, L. J., et al., supra). Thus, the preferred process for producing specific dihydronepetalactone enantiomers would be hydrogenation of an oil from a *Nepeta* chemotype known to contain specific nepetalactone stereoisomers.

The preferred process for producing the dihydronepetalactones represented by Formula I in the present invention, therefore, is by hydrogenation of nepetalactones from plants with oils of defined nepetalactone stereoisomer content, an industrially advantageous approach in terms of production cost and its biological basis. Other processes are as disclosed in U.S. Provisional Application No. 60/369,470, filed Apr. 3, 2002.

The dihydronepetalactones of the present invention possess unique properties of insect repellency and are particularly effective against a wide spectra of common insect pests, including biting insects, wood-boring insects, noxious insects, and household-pests.

The insect repellent compositions of this invention containing dihydronepetalactones or mixtures thereof are effective against a variety of insects which interfere with human society. These insects include a variety of biting insects (e.g., ants, bees, black flies, chiggers, fleas, green head flies, mosquitoes, stable flies, ticks, wasps), wood-boring insects (e.g., termites), noxious insects (e.g., houseflies, cockroaches, lice, roaches, wood lice), and household pests (e.g., flour and bean beetles, dust mites, moths, silverfish, weevils). In the case of mosquitoes, which convey pathogenic microbes, these repellent properties are additionally effective for preventing infection with such diseases.

A wide variety of compounds possess insect repellent and/or mosquito repellent activity, as evidenced by: 1.) the diversity of chemical structures reported by the USDA to contain repellent activity (Chemicals Evaluated as Insecticides and Repellents at Orlando, Fla., compiled by W. V. King, U.S. Department of Agriculture, Agricultural Research Service, Agriculture Handbook No. 69); and 2.) by the variety of insect repellant active materials present in insect repellent formations (See, e.g., European patent applications 97,812 and 97,813, and U.S. Pat. No. 4,127,672, U.S. Pat. No. 4,756,905, U.S. Pat. No. 5,465,685, U.S. Pat. No. 5,489,433, U.S. Pat. No. 5,565,208, U.S. Pat. No. 5,672,337 and U.S. Pat. No. 5,716,602). In general, activity is found in alcohols, amides, esters, ketones, acids, lactones, and lactams; and to some degree, repellency activity does appear to depend on the physical properties of these compounds.

One property that is important to overall insect repellency is surface activity, as most (if not all) repellents contain both polar and non-polar regions in their structure. A second property is volatility. Insect repellents form an unusual class of compounds where evaporation of the active ingredient from the host's skin surface or from the insect repellent article is necessary for effectiveness, as measured by the host's protection from insect bites or the article's protection from insect damage. In the case of a topical insect repellent, a certain minimum concentration of repellent is needed in the air space directly above the skin surface of the host in order to repel insects, and this concentration is a measure of the potency of the repellent. However, evaporation rate is also affected by the rate of skin absorption—in most cases, penetration into and through the skin is an undesirable mode of loss of compound from the skin surface. Similar considerations must be made for insect repellent articles, concerning the minimum concentration of repellent required in the three-dimensional air space surrounding the article itself.

A variety of strategies are available to researchers attempting to balance these properties of evaporation (and optionally, penetration). First, it is possible to find a single active ingredient having the right balance of physical properties. Alternatively, the active ingredient could be formulated with polymers and inert ingredients added to the active ingredient for the purpose of modifying the persistence of the active ingredient on the host's skin surface or within the insect repellent article. However, adding inert ingredients to the active ingredient limits the number of molecules of active ingredient on the surface of the repellent film or article. Since a molecule must be on the surface in order to evaporate, the evaporation rate is lowered. This carries with it the negative consequence of diluting the concentration of active ingredient that can be applied to the host's skin surface or that is present on the surface of an insect repellent article. This, in turn, reduces the overall potency of a formulation containing inert ingredients. In a third alternative, the active ingredient can be contained in microcapsules to control rates of loss from the host's skin surface or insect repellent article. Finally, another technique of limiting the evaporation rate of active ingredient is to synthesize a precursor molecule, which slowly disintegrates on the skin surface or insect repellent article to release the active ingredient.

For example, release of the active ingredient may be, for example, by sub-micron encapsulation, in which the active ingredient is encapsulated (surrounded) within a skin nourishing protein just the way air is captured within a balloon. The protein may be used at, for example, a 20% concentration. An application of repellent contains many of these protein capsules that are suspended in either a water-based lotion, or water for spray application. After contact with skin the protein capsules begin to breakdown releasing the encapsulated dihydronepetalactone. The process continues as each microscopic capsule is depleted then replaced in succession by a new capsule that contacts the skin and releases its active ingredient. The process may take up to 24 hours for one application. Because protein's adherence to the skin is so effective, these formulas are very resistant to perspiration (sweat-off), and water. When applied they are dry and comfortable with no greasiness. This system results in very effective protection, but it is only effective when used on skin because clothing does not have the capability to release the proteins. An alternative system uses a polymer to encase the repellent, which slows down early evaporation leaving more dihydronepetalactone available for later evaporation. This system can often increase a repellent's length of effectiveness by 25% to 50% over comparable non-entrapped products, but often feels greasy because of the presence of the polymer. In another alternative, a synergist is used to keep stimulating the evaporation of the dihydronepetalactone in the composition.

Regardless of the particular strategy applied to control volatility of an insect repellent, each repellent must have a minimum effective evaporation rate (MEER) from the skin surface or insect repellent article to maintain the necessary minimum concentration of repellent in the air space directly above the skin surface/article for effective insect repellency. An evaporation rate greater than the minimum effective evaporation rate (MEER) results in a significant and undesirable mode of loss. The issue is further complicated, however, since the MEER will change as a function of conditions in the field. Both the avidity or biting tendency of an insect and the concentration of insects in the host's environment must be considered. For example, as the avidity of mosquitoes increases, a higher MEER will be required. In an environment having a low concentration of mosquitoes where those mosquitoes are not hungry, the MEER could be as low as 2, or more commonly 5, or 6. In contrast, in an environment having a high concentration of hungry mosquitoes, the MEER might be as high as 12-15. Preferred in the present invention are insect compositions wherein the skin surface evaporation rate is at least equal to a minimum effective evaporation rate over a period of time where a preferred period of time is about 5 hours.

In the present invention, a variety of carriers or diluents for the above-disclosed dihydronepetalactones can be used. The carrier allows the formulation to be adjusted to an effective concentration of repellant molecules. When formulating a topical insect repellent, preferably, the repellant molecules are mixed in a dermatologically acceptable carrier. The carrier may further provide water repellency, prevent skin irritation, and/or soothe and condition skin. Factors to consider when selecting a carrier(s) for any formulation of insect repellent include commercial availability, cost, repellency, evaporation rate, odor, and stability. Some carriers can themselves have repellent properties.

For the present invention, the specific choice of a carrier, if any, to be utilized in achieving the desired intimate admixture with the final product can be any carrier conventionally used in insect repellent formulations. The carrier, moreover, should preferably also be one that will not be harmful to the environment. Accordingly, the carrier can be any one of a variety of commercially available organic and inorganic liquid, solid, or semi-solid carriers or carrier formulations usable in formulating insect repellent products. For example the carrier may include silicone, petrolatum, lanolin or many of several other well known carrier components.

Examples of organic liquid carriers include liquid aliphatic hydrocarbons (e.g., pentane, hexane, heptane, nonane, decane and their analogs) and liquid aromatic hydrocarbons. Examples of other liquid hydrocarbons include oils produced by the distillation of coal and the distillation of various types and grades of petrochemical stocks, including kerosene oils which are obtained by fractional distillation of petroleum. Other petroleum oils include those generally referred to as agricultural spray oils (e.g., the so-called light and medium spray oils, consisting of middle fractions in the distillation of petroleum and which are only slightly volatile). Such oils are usually highly refined and may contain only minute amounts of unsaturated compounds. Such oils, moreover, are generally paraffin oils and accordingly can be emulsified with water and an emulsifier, diluted to lower concentrations, and used as sprays. Tall oils, obtained from sulfate digestion of wood pulp, like the paraffin oils, can similarly be used. Other organic liquid carriers can include liquid terpene hydrocarbons and terpene alcohols such as alpha-pinene, dipentene, terpineol, and the like.

Other carriers include silicone, petrolatum, lanolin, liquid hydrocarbons, agricultural spray oils, paraffin oil, tall oils, liquid terpene hydrocarbons and terpene alcohols, aliphatic and aromatic alcohols, esters, aldehydes, ketones, mineral oil, higher alcohols, finely divided organic and inorganic solid materials.

In addition to the above-mentioned liquid hydrocarbons, the carrier can contain conventional emulsifying agents which can be used for causing the dihydronepetalactone compounds to be dispersed in, and diluted with, water for end-use application.

Still other liquid carriers can include organic solvents such as aliphatic and aromatic alcohols, esters, aldehydes, and ketones. Aliphatic monohydric alcohols include methyl, ethyl, normal-propyl, isopropyl, normal-butyl, sec-butyl, and tert-butyl alcohols. Suitable alcohols include glycols (such as ethylene and propylene glycol) and pinacols. Suitable polyhydroxy alcohols include glycerol, arabitol, erythritol, sorbitol, and the like. Finally, suitable cyclic alcohols include cyclopentyl and cyclohexyl alcohols.

Conventional aromatic and aliphatic esters, aldehydes and ketones can be used as carriers, and occasionally are used in combination with the above-mentioned alcohols. Still other liquid carriers include relatively high-boiling petroleum products such as mineral oil and higher alcohols (such as cetyl alcohol). Additionally, conventional or so-called "stabilizers" (e.g., tert-butyl sulfinyl dimethyl dithiocarbonate) can be used in conjunction with, or as a component of, the carrier or carriers comprising the compositions of the present invention.

Solid carriers which can be used in the compositions of the present invention include finely divided organic and inorganic solid materials. Suitable finely divided solid inorganic carriers include siliceous minerals such as synthetic and natural clay, bentonite, attapulgite, fuller's earth, diatomaceous earth, kaolin, mica, talc, finely divided quartz, and the like, as well as synthetically prepared siliceous materials, such as silica aerogels and precipitated and fume silicas. Examples of finely divided solid organic materials include cellulose, sawdust, synthetic organic polymers, and the like. Examples of semi-solid or colloidal carriers include waxy solids, gels (such as petroleum jelly), lanolin, and the like, and mixtures of well-known liquid and solid substances which can provide semi-solid carrier products, for providing effective repellency within the scope of the instant invention.

Insect repellent compositions of the present invention containing the dihydronepetalactones may also contain adjuvants known in the art of personal care product formulations, such as thickeners, buffering agents, chelating agents, preservatives, fragrances, antioxidants, gelling agents, stabilizers, surfactants, emolients, coloring agents, aloe vera, waxes, other penetration enhancers and mixtures thereof, and therapeutically or cosmetically active agents.

Additionally, the compositions of the present invention may also contain other adjuvants such as one or more therapeutically or cosmetically active ingredients. Exemplary therapeutic or cosmetically active ingredients useful in the compositions of the invention include fungicides, sunscreening agents, sunblocking agents, vitamins, tanning agents, plant extracts, anti-inflammatory agents, anti-oxidants, radical scavenging agents, retinoids, alpha-hydroxy acids, emollients, antiseptics, antibiotics, antibacterial agents or antihistamines, and may be present in an amount effective for achieving the therapeutic or cosmetic result desired.

Dihydronepetalactones may be utilized in the present invention individually or combined in any proportion. As is conventional in the art, the desired amount of an insect repellent composition to be added to a given insect susceptible article with properties of insect repellency is determined by the nature of the product and other factors. These factors include both considerations of cost and the nature of the other ingredients in the insect repellent composition or repellent article, their amounts, and the desired repellency effect. In general, the composition of the repellent should contain sufficient amounts of active insect repellant material to be efficacious in repelling the insect from the host over a prolonged period of time (preferably, for a period of at least several hours).

The amount of each dihydronepetalactone of Formula I or mixtures thereof in an insect repellent composition or repellent article in accordance with the present invention will generally not exceed about 80% by weight based on the weight of the final product, however, greater amounts may be utilized in certain applications and this amount is not limiting. More preferably, a suitable amount of dihydronepetalactone will be at least about 0.001% by weight and preferably about 0.01% up to about 50% by weight; and more preferably, from about 0.01% to about 20% weight percent, based on the weight of the composition or article. Specific compositions will depend on the intended use.

The dihydronepetalactone repellent compositions of the present invention can be formulated without a carrier and be effective. More often, however, the insect repellent composition will include a carrier and contain about 0.001-50% weight of the disclosed compounds, and such compound is usually in intimate mixture with the carrier to bring the active material into position for repelling common insect pests, such as biting insects, wood-boring insects, noxious insects, household pests, and the like.

The compositions of the invention may be formulated and packaged so as to deliver the product in a variety of forms including as a solution, suspension, cream, ointment, gel, film or spray, depending on the preferred method of use. The carrier may be an aerosol composition adapted to disperse the dihydronepetalactone into the atmosphere by means of a compressed gas.

In some cases, the dihydronepetalactone repellent compositions of the present invention can be formulated with at least one other insect repellent that is not itself dihydronepetalactone to create a potentiated insect repellent composition (see, for example, U.S. Pat. No. 4,869,896). In this case, the effect of the dihydronepetalactone and the at least one other insect repellent produce a repellency result substantially in excess of that which reasonably could be expected or predicted from the known effect of the components either alone or additively. Exemplary other insect repellent compounds which may be used in a potentiated insect repellent composition with dihydronepetalactones include, but are not limited to: benzil; benzyl benzoate; 2,3,4,5-bis(butyl-2-ene)tetrahydrofurfural(MGK Repellent 11); butoxypolypropylene glycol; N-butylacetanilide; normal-butyl-6,6-dimethyl-5,6-dihydro-1,4-pyrone-2-carboxylate (Indalone); dibutyl adipate; dibutyl phthalate; di-normal-butyl succinate (Tabatrex); N,N-diethyl-meta-toluamide (DEET); dimethyl carbate (endo,endo)-dimethyl bicyclo[2.2.1]hept-5-ene-2,3-dicarboxylate); dimethyl phthalate; 2-ethyl-2-butyl-1,3-propanediol; 2-ethyl-1,3-hexanediol (Rutgers 612); di-normal-propyl isocinchomeronate (MGK Repellent 326); 2-phenylcyclohexanol; normal-propyl N,N-diethylsuccinamate, 1-piperidinecarboxylic acid 2-(2-hydroxymethyl) 1-methylpropylester (Bayrepel) and p-menthane-3,8-diol. Preferred is a potentiated insect repellent composition comprising dihydronepetalactones (or a mixture thereof) and DEET, Bayrepel or p-menthane-3,8-diol. Most preferred is a potentiated insect repellent composition comprising dihydronepetalactones (or a mixture thereof) and other natural repellent molecules such as p-menthane-3,8-diol.

Desirable properties of a topical insect repellent article include low toxicity, resistance to loss by water immersion or sweating, low or no odor or at least a pleasant odor, ease of application, and rapid formation of a dry tack-free surface film on the host's skin. In order to obtain these properties, the formulation for a topical insect repellent article should permit insect-infested animals (e.g., dogs with fleas, poultry with lice, cows with ticks, and humans) to be treated with an insect repellent composition of the present invention by contacting the skin, fur or feathers of such an animal with an effective amount of the repellent article for repelling the insect from the animal host. Thus, dispersing the article into the air or dispersing the composition as a liquid mist or fine dust will permit the repellent composition to fall on the desired host surfaces. Likewise, directly spreading of the liquid/semi-solid/solid repellent article on the host is an effective method of contacting the surface of the host with an effective amount of the repellent composition.

Embodiments of the present invention which may be used as a topical insect repellent articles, include (but are not limited to): colognes, lotions, sprays, creams, gels, ointments, bath and shower gels, foam products (e.g., shaving foams), makeup, deodorants, shampoo, hair lacquers/hair rinses, and personal soap compositions (e.g., hand soaps and bath/shower soaps).

This invention also relates to the use of dihydronepetalactone mixtures as insect repellents in a variety of articles which are susceptible to attack by insects. These outdoor consumable products will generally, but not necessarily, comprise an insect repellent composition of the invention, but will contain an effective amount of dihydronepetalactone. Typical articles that can be improved by the use of dihydronepetalactones and mixtures thereof include, but are not limited to: air fresheners, candles, other scented articles, fibers, sheets, cloth [e.g., for clothing, nettings (mosquito netting), and other fabrics], paper, paint, ink, clay, woods, furniture (e.g., for patios and decks), carpets, sanitary goods, plastics, polymers, and the like.

The dihydronepetalactone compositions of this invention may be blended with polymers, which may also involve a controlled release systems. Compatible polymers may or may not be biodegradable. Exemplary polymers are high density polyethylene or low density polyethylene, biodegradable thermoplastic polyurethanes, biodegradable ethylene polymers, and poly(epsilon caprolactone) homopolymers and compositions containing the same as disclosed in U.S. Pat. No. 4,496,467, U.S. Pat. No. 4,469,613 and U.S. Pat. No. 4,548,764.

Dihydronepetalactones are particularly advantageous for use as repellent materials in preparations of the present invention for a variety of reasons.

First, the compounds are cost effective to produce, an important consumer consideration when choosing an effective repellent. Many commerically available repellent products are only effective in relatively concentrated form, including as much as 5-30% (or more) repellent in a carrier, based on total weight. U.S. Pat. No. 4,416,881 to McGovern et al., for example, discloses repellent concentrations of 6.25-25% repellent in a carrier.

Secondly, the compounds are known natural compounds, thus overcoming concerns raised against synthetic chemicals such as DEET as the primary active ingredient in repellent compositions.

Finally, in addition to the natural repellent properties of the dihydronepetalactone mixtures thus prepared, the compositions also possess a unique and pleasant fragrance. The fragrance notes of the subject compounds make them useful in imparting, altering, augmenting or enhancing the overall olfactory component of an insect repellent composition or article, for example, by utilizing or moderating the olfactory reaction contributed by one or more other ingredients in the composition. Specifically, the dihydronepetalactones of the invention or mixtures thereof may be utilized to either mask or modify the odor contributed by other ingredients in the formulation of the final repellent composition or article, and/or to enhance consumer appeal of a product by imparting a characteristic perfume or aroma. It is expected that the pleasant fragrance of dihydronepetalactones will possess much greater appeal to consumers than other insect repellent compounds, particularly DEET.

Dihydronepetalactones and their uses are also described in U.S. Ser. No. 10/349,865, filed Jan. 23, 2003, which is incorporated in its entirety as a part hereof for all purposes.

EXAMPLES

The present invention is further defined in the following examples. It should be understood that these examples, while indicating preferred embodiments of the invention, are given by way of illustration only. From the above discussion and these examples, one skilled in the art can ascertain the essential characteristics of this invention, and without departing from the spirit and scope thereof, can make various changes and modifications of the invention to adapt it to various usages and conditions. The notation below of w/v refers to the weight of the active ingredient in grams in 100 mL of solution.

The meaning of abbreviations is as follows: "h" means hour(s), "min" means minute(s), "sec" means second(s), "d" means day(s), "mL" means milliliters, "L" means liters, "m/z" means mass (m) to charge (z) ratio, "ppm" means parts per million, "mol %" means percentage expressed on a molar basis, "Hz" means Hertz (1/sec), and "psig" means pounds per square inch guage.

Example 1

Preparation of Nepetalactones by Fractional Steam Distillation of Oil of *Nepeta cataria*

A sample of commercially-available catnip oil, prepared by steam distillation of herbaceous material from the catmint *Nepeta cataria*, was obtained (Berjé, Bloomfield, N.J., USA). Combined gas chromatography—mass spectrometry (GC-MS) of this oil indicated that the principal constituents were nepetalactone stereoisomers (data not shown).

Figure 2:
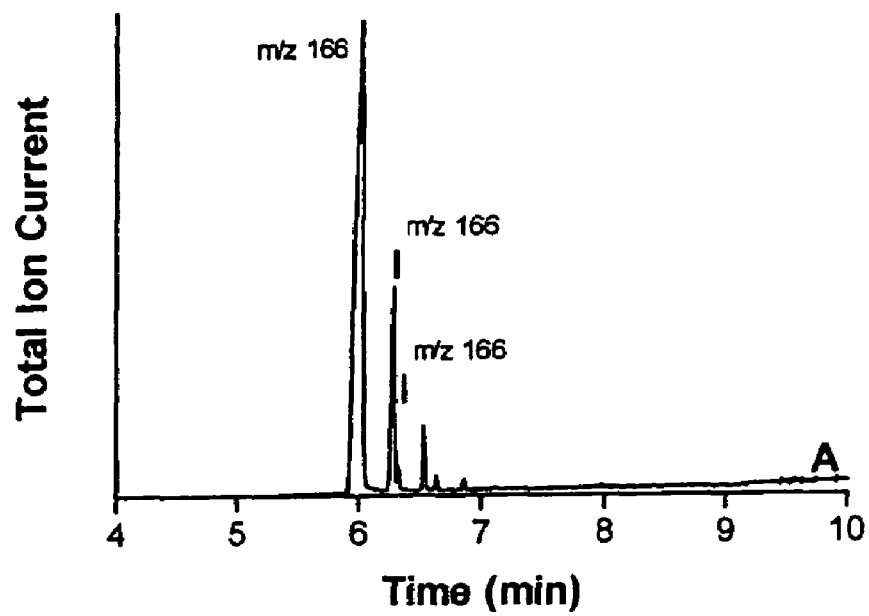
FIG. 2 shows the total ion chromatograms from combined gas chromatography/mass spectrometry (GC-MS) analysis of a distilled nepetalactone-enriched fraction from commercially-available catmint oil (A), together with that of the material produced from this fraction by hydrogenation (B).
Figure 2:
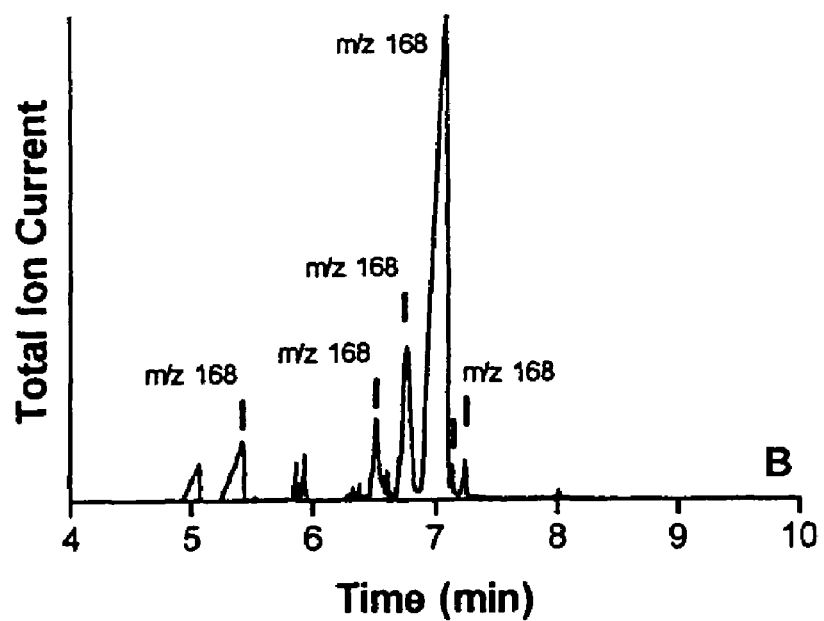
Figure 3:
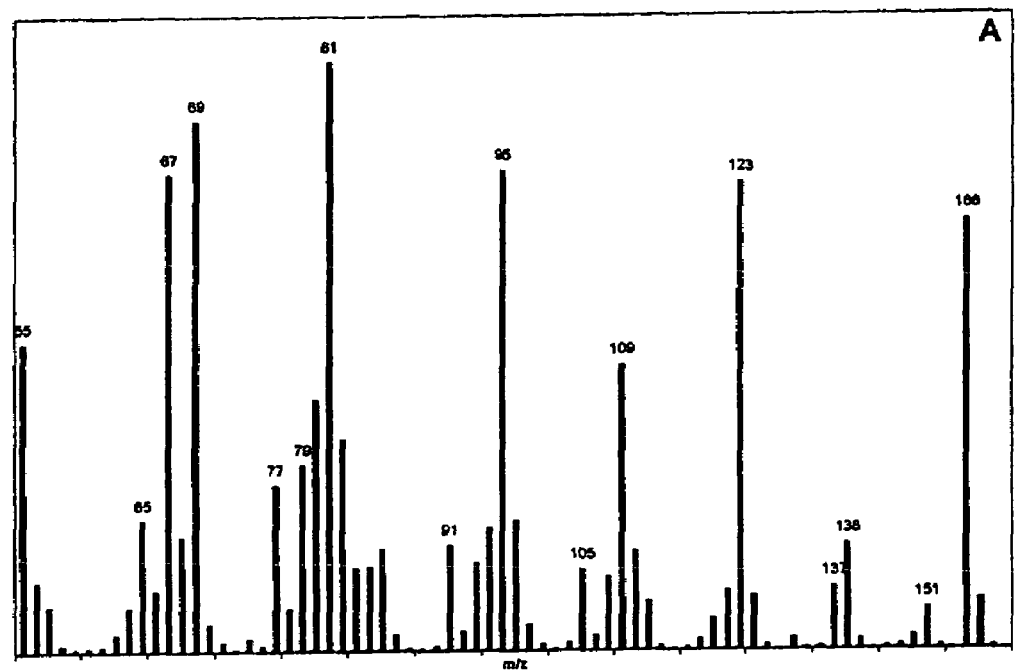
FIG. 3 shows the mass spectra of the major constituents of the nepetalactone-enriched fraction (A) and the hydrogenated material (B) identified by GC-MS analysis.
Figure 3:
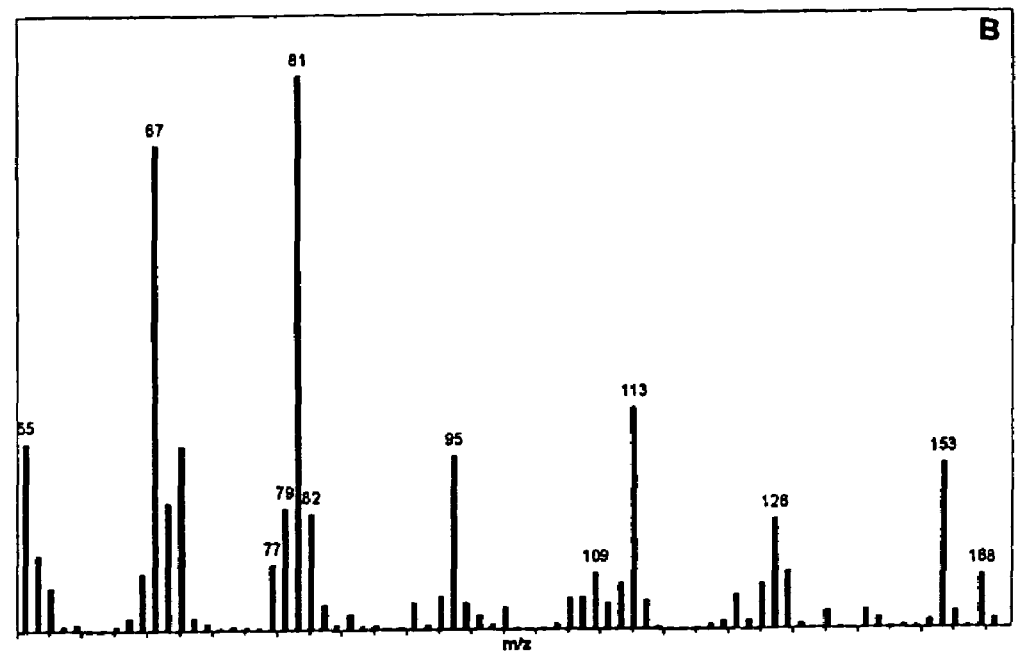
Figure 4:
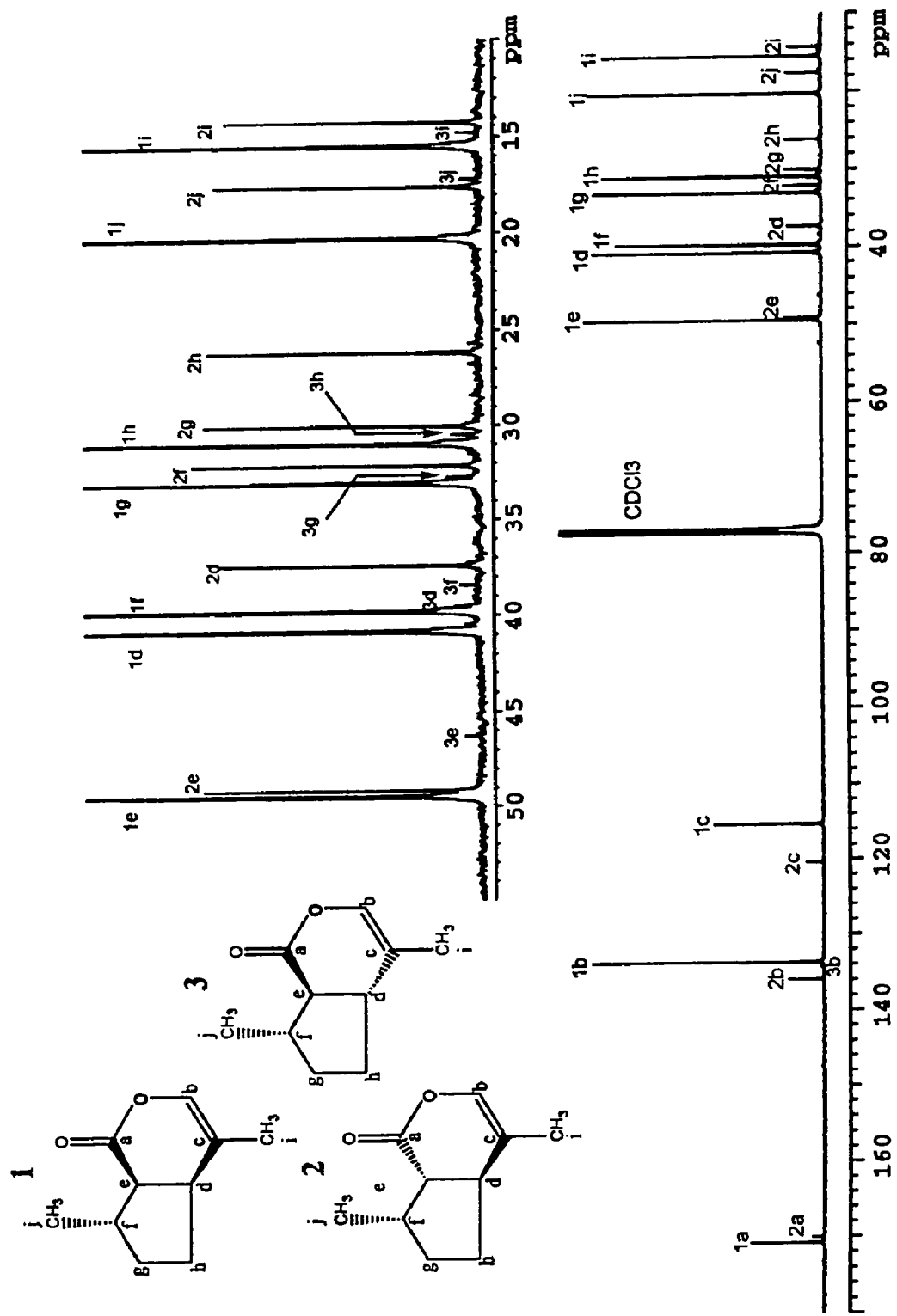
FIG. 4 shows the $^{13}C$ NMR analysis performed on a distilled nepetalactone-enriched fraction of commercially-available catmint oil.

The nepetalactone fraction was further purified by fractional distillation of this oil. FIG. 2A presents the GC-MS total ion chromatogram of the nepetalactone-enriched fraction prepared by fractional distillation of the commercial sample of *Nepeta cataria* essential oil. The conditions employed were: column HP5-MS, 25 m×0.2 mm; oven 120° C., 2 min, 15° C./min, 210° C., 5 min.; He@ 1 ml/min. Peaks with m/z 166 are nepetalactones). The unlabelled peaks correspond to minor sesquiterpenoid contaminants. In FIG. 3A, the mass spectrum of the major peak (6.03 min, nepetalactone) in FIG. 2A is shown. $^1H$ and $^{13}C$ NMR analysis of the oil and the purified material was also carried out, and the $^{13}C$ data is presented (FIG. 4). The $^{13}C$ chemical shifts for the four possible stereoisomers reported in the literature were compared to the spectra taken for the sample. Three stereoisomers were detected and the amounts were quantified based on the carbonyl region at around 170 ppm. The chemical shifts, for both the original oil and the enriched material, are provided in Table 1. Each carbon atom of nepetalatone is identified, as shown in FIG. 4.

TABLE 1

$^{13}$C Chemical Shifts and Mol % Values of
Nepetalactone Stereoisomers Present in Commercial Sample of
Essential Oil of Catmint (*Nepeta cataria*) and in
Fraction Purified by Steam Distillation

| ATOM | ESSENTIAL OIL | | | PURIFIED FRACTION | | |
|---|---|---|---|---|---|---|
| | cis, trans- δ (ppm) | trans, cis- δ (ppm) | cis, cis- δ (ppm) | cis, trans- δ (ppm) | trans, cis- δ (ppm) | cis, cis- δ (ppm) |
| a | 170.9 | 170.1 | | 170.8 | 170.1 | |
| b | 133.7 | 135.9 | 134.2 | 133.7 | 135.9 | 134.2 |
| c | 115.3 | 120.4 | | 115.3 | 120.4 | |
| d | 40.8 | 37.3 | 39.6 | 40.8 | 37.4 | 39.5 |
| e | 49.4 | 49.1 | 46.4 | 49.5 | 49.1 | 46.3 |
| f | 39.7 | 32.1 | 38.4 | 39.8 | 32.1 | 38.4 |
| g | 33.0 | 30.0 | 32.7 | 33.1 | 30.0 | 32.7 |
| h | 30.9 | 26.1 | 30.4 | 31.0 | 26.1 | 30.5 |
| j | 20.2 | 17.5 | 17.1 | 20.3 | 17.6 | 17.2 |
| i | 15.4 | 14.2 | 14.7 | 15.5 | 14.2 | 14.8 |
| Mol % | 80.20% | 17.70% | 2.10% | 84.50% | 14.30% | 1.20% |

This analysis indicated that in the oil, nepetalactones were present in the following proportions: 80.2 mol % cis,trans-nepetalactone, 17.7 mol % trans,cis-nepetalactone and 2.1 mol % cis,cis-nepetalactone. The data indicated the proportions of nepetalactones in the purified material were 84.5 mol % cis,trans-nepetalactone, 14.3 mol % trans,cis-nepetalactone and 1.2 mol % cis,cis-nepetalactone. GC-MS analysis of this purified fraction indicated that it consisted predominantly of these nepetalactones (m/z 166), accompanied by trace amounts of the sesquiterpenoids caryophyllene and humulene (data not shown).

Example 2

Preparation of Dihydronepetalactones 107 g of the distilled nepetalactone fraction of the catmint oil prepared as described in Example 1 was dissolved in ethanol (200 ml) and placed in a Fisher-Porter bottle with 12.7 g 2% Pd/SrCO$_3$ (Aldrich 41,461-1). The tube was evacuated and backfilled with H$_2$ two times, then charged with H$_2$ at 30 psig. After 48 hr stirring at room temperature, the tube was vented and the contents filtered over Celite to remove catalyst. The solvent was removed under vacuum, yielding a clear oil.

GC-MS analysis (column HP5-MS, 25 m×0.2 mm; Oven 120° C., 2 min, 15° C./min, 210° C., 5 min.; He@ 1 ml/min) was conducted on this material. The total ion chromatogram is presented in FIG. 2B. This analysis indicated that the principal component (65.43% area; Rt 7.08 min) represented a dihydronepetalactone isomer, with m/z 168; the mass spectrum of this component is presented in FIG. 3B. This spectrum contains an ion with m/z 113, diagnostic for dihydronepetalactones (Jefson, M., et al. *J. Chemical Ecology* 9:159-180 (1983)). Five additional peaks, representing the remaining dihydronepetalactone diastereomers which might be derived from the three nepetalactones present in the starting material were also represented in the chromatogram. These occurred at Rt 5.41 min, 6.8% area, m/z 168; Rt 5.93 min, area 1.2%, m/z 168; Rt 6.52 min, 4.88% area, mass 168; Rt 6.76 min, 13.8% area, m/z 168 and Rt 7.13 min, 1.25% area, m/z 168. No residual nepetalactones were detected by GC-MS.

Figure 5:
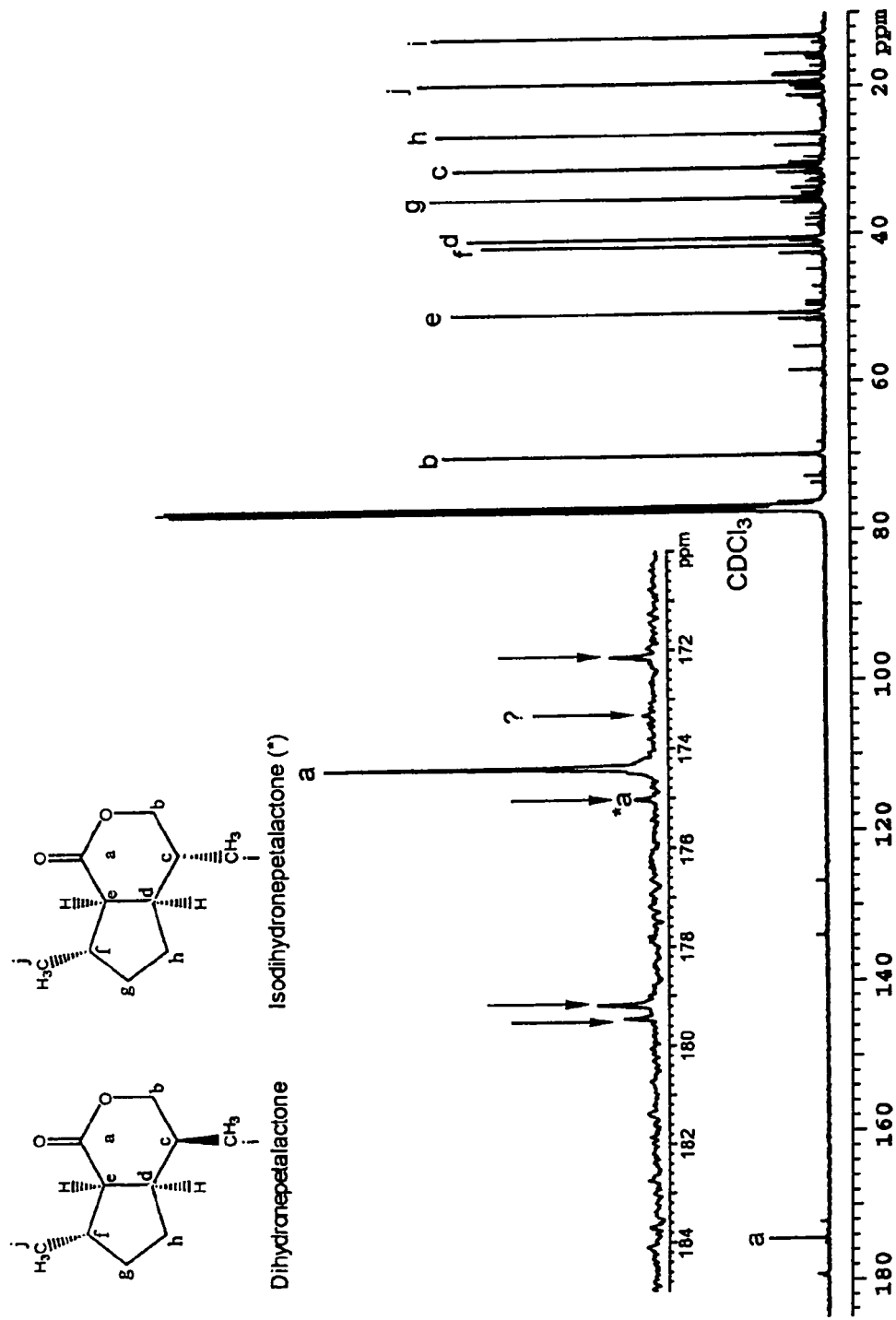
FIG. 5 shows the $^{13}C$ NMR spectrum obtained from analysis of the dihydronepetalactones produced by hydrogenation of a distilled nepetalactone-enriched fraction of commercially-available catmint oil.

$^1$H, $^{13}$C and a series of 2D NMR analyses were also performed. The carbonyl region of the $^{13}$C NMR spectrum (FIG. 5) showed at least five spin systems, one of them in larger amounts than the other four (ca. 75%). Very little residual nepetalactone was detected.

Based on the analysis of coupling constants and the intensities of the different NOE cross peaks observed, the stereochemistry of the principal component of the material was determined to be the dihydronepetalactone of Formula 2 (9S,5S,1R,6R)-5,9-dimethyl-3-oxabicyclo[4.3.0]nonan-2-one).

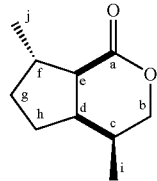

Formula 2

The distance between the methyl group (i) and proton (d) is longer than the distance between the methyl group (j) and the proton (e), an observation consistent with the cis-trans stereochemical configuration.

The stereoisomer isodihydronepetalactone(9S,5R, 1R,6R)-5,9-dimethyl-3-oxabicyclo[4.3.0]nonan-2-one; (Formula 3) was similarly identified by $^{13}$C chemical shifts and is present in 3.6%.

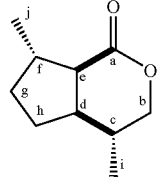

Formula 3

Thus the GC-MS and NMR data indicate that hydrogenation of the mixture of nepetalactone stereoisomers yielded the corresponding dihydronepetalactone diastereomers, as expected. The pair of diastereomers (Formula 2 and Formula 3) derived from cis,trans-nepetalactone (84.5 Mol % of the starting material) were the predominant dihydronepetalactones, at 78.6% of the mixture following hydrogenation.

Example 3

Repellency Testing of a Dihydronepetalactone Mixture

The dihydronepetalactone mixture prepared in accordance with Example 2 was evaluated for its repellent effects against female *Aedes aegypti* mosquitoes. These tests were carried out under contract by Insect Control & Research, Inc. (Baltimore, Md.).

Approximately 250 female *Aedes aegypti* mosquitoes were introduced into a chamber containing 5 wells, each covered by a Baudruche membrane. Wells were filled with bovine blood, containing sodium citrate (to prevent clotting) and ATP (72 mg ATP disodium salt per 26 ml of blood), and heated to 37° C. A volume of 25 μl of isopropyl alcohol, containing putative repellent chemicals (Table 2), was applied to each membrane.

TABLE 2

Experimental Design Applied for Repellency Testing

| Purpose | Compound | Concentration |
|---|---|---|
| Untreated Control | Isopropyl alcohol | 100% |
| Positive Control | Isopropyl alcohol with DEET | 1.0% (w/v) |
| Experimental Samples | Isopropyl alcohol with Dihydronepetalactone | 1.0% (w/v) |
| | | 2.5% (w/v) |
| | | 5.0% (w/v) |

After 5 min, 4 day-old female mosquitoes were added to the chamber. The number of mosquitoes probing the membranes for each treatment was recorded at 2 min intervals over 20 min. All data presented is from three replicate experiments.

Table 3 presents the effect of dihydronepetalactone concentration with respect to the amount of time taken before the female *A. aegypti* mosquitoes first probed each membrane.

TABLE 3

Effect of Dihydronepetalactone Concentration on Mean Time to "First Probing"

| Repellent Concentration | Mean Time (min) |
|---|---|
| Isopropyl alcohol (untreated control) | 4.6 |
| 1% DEET (positive control) | 12 |
| 1% DHN | 8 |
| 2.5% DHN | 9.3 |
| 5% DHN | 18 |

Mosquitoes began landing on the untreated control well within 4.6 min. Dihydronepetalactone at 5% concentration was found to discourage mosquito "first probing" for approximately 18 min, compared to 12 min for DEET (at 1% w/v). Lower concentrations of dihydronepetalactone (1% and 2.5% w/v) were found to inhibit first probing for an average of 8 and 9.3 min, respectively.

Figure 6:
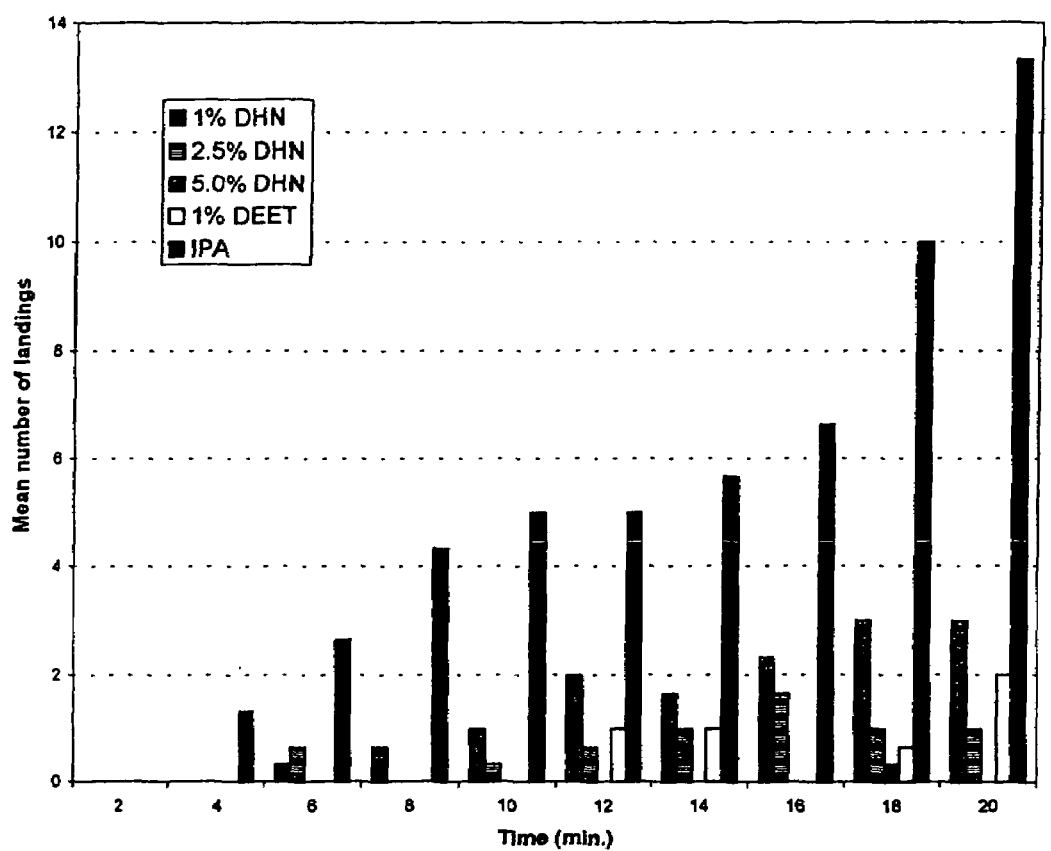
FIG. 6 shows the distribution of landing density of female *Aedes aegyptii* mosquitoes on membranes treated with dihydronepetalactones over time in an in vitro repellency test in Example 3.

The distribution of landing density by female *A. aegypti* on membranes treated with dihydronepetalactones was analyzed over time, as shown graphically in FIG. 6. Dihydronepetalactone at 5% concentration was found to almost eliminate mosquito landings for 20 minutes, while. DEET (1% w/v) permitted 2 mosquitoes to land in this experiment. Again, lower concentrations of dihydronepetalactone (1% and 2.5% w/v) were found to exhibit repellency (as compared to the untreated control), but at lower levels than the positive control (DEET at 1% w/v).

The total number of landings permitted on each membrane during the course of the experiments were determined, and the results are summarized in Table 4.

TABLE 4

Number of Landings Permitted According to Repellency Concentration

| Repellent Concentration | Mean Number of Landings |
|---|---|
| Isopropyl alcohol (untreated control) | 58.99 |
| 1% DEET (positive control) | 4.66 |
| 1% DHN | 14 |
| 2.5% DHN | 6.33 |
| 5% DHN | 0.33 |

Again, the data shows that at all concentrations tested dihydronepetalactone was repellent, although significantly increased repellency with respect to 1% DEET was observed only at 5% (w/v).

Cumulatively, this data show that at all three concentrations tested, treatment with dihydronepetalactone significantly reduced probing of the membranes over the course of the experiment (20 min) as compared to the isopropyl alcohol treatment. At concentrations of 2.5% and 5.0%, dihydronepetalactones had effectiveness as a repellent of mosquitoes for the entire observation period. There was also a direct relationship between dihydronepetalactone concentration and the time elapsed for the first mosquito to land and begin probing the membrane. Overall, the data indicates that the mixture of dihydronepetalactones employed in these experiments was an effective repellent, although repellency equivalent to DEET was observed only with higher concentrations.

Example 4

Preparation of Dihydronepetalactones from trans,cis-nepetalactone

It has been shown that trans,cis-nepetalactone ($4aS$, $7S$, $7aS$— or E,Z-nepetalactone), is more effective than either the cis,trans-(Z,E-) nepetalactone or unfractionated catmint essential oil in repelling the german cockroach (Peterson, C. J. et al. (2002) *Household and Structural Insects*, 95 (2), 377-380). Accordingly, we determined to purify trans,cis-nepetalactone for hydrogenation to the corresponding dihydronepetalactones and repellency testing of these derivatives. A number of plants were grown from seed of the catmint *Nepeta racemosa* (Chiltern Seeds, Cumbria, UK). Leaf pairs plucked from individual plants were immersed in ethyl acetate and after 2 h the solvent was removed and the extracts analyzed by gas chromatography. Plants producing preponderantly trans,cis-nepetalactone in their oils were thus identified (Clark, L. J., et al. (1997) *The Plant Journal*, 11:1387-1393), and grown to maturity. Leaf material from these plants was harvested, freeze-dried, extracted into ethyl acetate, and the extracts concentrated. Nepetalactone was purified from the concentrated extract by silica gel chromatography in hexane/ethyl acetate (9:1) followed by preparative thin-layer chromatography on silica using the same solvent mixture. After removal of the solvent and re-dissolving in hexane, the trans,cis-nepetalactone was crystallized on dry ice. GC-MS and NMR ($^1$H and $^{13}$C) analysis confirmed the identity of the crystalline material as trans, cis-nepetalactone. The $^{13}$C chemical shifts, compared to the chemical shifts of Table 1, are shown in Table 5.

TABLE 5

$^{13}$C chemical shifts of the nepetalactone sample prepared in Example 4, compared to the chemical shifts of trans, cis-nepetalactone (from Table 1)

| Atom | trans, cis-nepetalactone δ (ppm) | Sample δ (ppm) |
|---|---|---|
| a | 170.1 | 170.3 |
| b | 135.9 | 136.0 |
| c | 120.4 | 120.5 |
| d | 37.3 | 37.5 |
| e | 49.1 | 49.3 |
| f | 32.1 | 32.2 |
| g | 30.0 | 30.1 |

TABLE 5-continued $^{13}$C chemical shifts of the nepetalactone sample prepared in
Example 4, compared to the chemical shifts of trans, cis-nepetalactone
(from Table 1)

| Atom | trans, cis-nepetalactone δ (ppm) | Sample δ (ppm) |
|---|---|---|
| h | 26.1 | 26.3 |
| j | 17.5 | 17.7 |
| i | 14.2 | 14.4 |

Hydrogenation of the trans,cis-nepetalactone thus prepared was carried out in ethanol using ESCAT#142 catalyst (Englehart) at 50° C. for 4h. GC-MS and NMR ($^1$H and $^{13}$C) confirmed that the trans,cis-nepetalactone had been quantitatively converted to the corresponding dihydronepetalactone stereoisomers, with one in significant excess. NMR analysis of the major diastereomer: $^1$H NMR (500 MHz, CDCl$_3$): d 0.97 (d, 3H, J=6.28 Hz), 0.98 (d, 3H, J=6.94 Hz) d 1.24 (m, 2H), 1.74 (m, 1H), 1.77 (m, 2H), 1.99 (m, 2H), 2.12 (dd, 1H, J=6.86 and 13.2 Hz), 2.51 (m, 1H), 3.78 (tr, 1H, J=11.1 Hz), 4.33 (dd, 1H, J=5.73 and 11.32 Hz); $^{13}$C (500 MHz, CDCl$_3$): d 15.43, 18.09, 27.95, 30.81, 31.58, 35.70, 42.51, 51.40, 76.18, 172.03. The $^{13}$C NMR spectrum indicated that this major diastereomer constituted ca. 93.7% of the preparation. Based on the observed couplings for the methylene to the lactone oxygen, the stereogenic methine carbon bearing methyl group, the methyl group itself and the bridgehead methine, it is concluded that the diastereomer is most likely the (1S,9S,5R,6R)-5,9-dimethyl-3-oxabicyclo[4.3.0]nonan-2-one) of Formula 4.

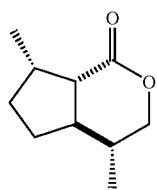

Formula 4

The magnitude of the observed couplings are consistent with dihedral angles between the protons on vicinal carbon atoms in the above structure according to the Karplus equation (ref. Spectrophotometric Identification of Organic Compounds, 4th. edition, Robert M. Silverstein, G. Clayton Bassler and Terence C. Morill, 1981, page 208-210).

Example 5

Repellency Testing of Dihydronepetalactones Prepared by Hydrogenation of trans,cis-Nepetalactone The dihydronepetalactone prepared according to Example 4, consisting predominantly of 1S,9S,5R,6R-5,9-dimethyl-3-oxabicyclo[4.3.0]nonan-2-one; Formula 4, was tested for repellency against *Aedes aegypti* mosquitoes essentially as described in Example 3. The experimental design is summarized in Table 6, and all data presented is from five replicate experiments.

TABLE 6

Experimental Design Applied for Repellency Testing

| Purpose | Compound | Concentration |
|---|---|---|
| Untreated Control | Isopropyl alcohol | 100% |
| Positive Control | Isopropyl alcohol with DEET | 1.0% (w/v) |
| Experimental Samples | Isopropyl alcohol with Dihydronepetalactone | 1.0% (w/v) 0.5% (w/v) 0.2% (w/v) |

Table 7 presents the effect of dihydronepetalactone concentration with respect to the amount of time taken before the female *A. aegyptii* mosquitoes first probed each membrane.

TABLE 7

Effect of Dihydronepetalactone Concentraton on Mean Time to "First Probing"

| Repellent Concentration | Mean Time (min) |
|---|---|
| Isopropyl alcohol (untreated control) | 8.0 |
| 1% DEET (positive control) | 14.8 |
| 1% DHN | 16.0 |
| 0.5% DHN | 10.4 |
| 0.2% DHN | 8.4 |

Dihydronepetalactone at 1% concentration was found to discourage mosquito "first probing" for approximately 16 min, marginally better than (but statistically indistinguishable from) DEET at the same concentration, where mean time to first probe was 14.8 min. Lower concentrations of dihydronepetalactone (0.5% and 0.2% w/v) were found to inhibit first probing for an average of 10.4 and 8.4 min, respectively.

Figure 7:
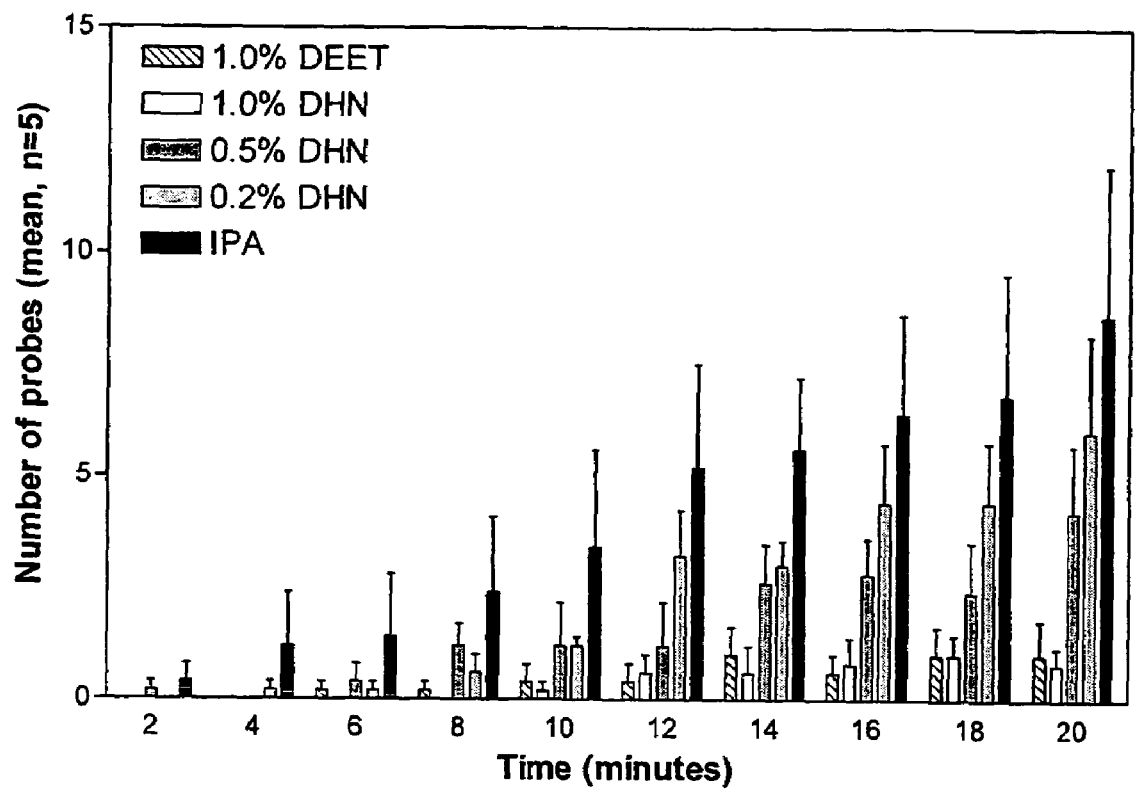
FIG. 7 shows the distribution of landing density of female *Aedes aegyptii* mosquitoes on membranes treated with dihydronepetalactones over time in an in vitro repellency test in Example 5.

The distribution of landing density by female *A. aegypti* on membranes treated with dihydronepetalactones was analyzed over time, as shown graphically in FIG. 7. Dihydronepetalactone at 1.0% concentration was found to completely eliminate mosquito landings for 10 minutes, while DEET (1% w/v) permitted mosquitoes to land by 8 min. Again, lower concentrations of dihydronepetalactone (0.5% and 0.2% w/v) were found to exhibit repellency (as compared to the untreated control), but at lower levels than the positive control (DEET at 1% (w/v)).

The total number of landings permitted on each membrane during the course of the experiments were determined, and the results are summarized in Table 8.

TABLE 8

Number of Landings Permitted According to Repellent and Concentration During 2 minute Observation Periods

| Repellent Concentration | Mean Number of Landings |
|---|---|
| Isopropyl alcohol (untreated control) | 18.17 |
| 1% DEET (positive control) | 4.8 |
| 1% DHN | 4.0 |
| 0.5% DHN | 16.2 |
| 0.2% DHN | 23.2 |

Again, this data indicates that 1% dihydronepetalactone exhibited equivalent repellent activity to 1% DEET.

Cumulatively, this data show that at all three concentrations tested, treatment with dihydronepetalactone significantly reduced probing of the membranes over the course of the experiment (20 min) as compared to the isopropyl alcohol treatment. At all concentrations tested, dihydronepetalactones had effectiveness as a repellent of mosquitoes for the entire observation period. There was also a direct relationship between dihydronepetalactone concentration and the time elapsed for the first mosquito to land and begin probing the membrane. Overall, the data indicate that the dihydronepetalactones derived from hydrogenation of trans,cis-nepetalactone are an effective repellent, and equivalent to DEET in efficacy in these tests.

What is claimed is:

1. A method of repelling an insect or tick from a host for the insect or tick, wherein the host is a human or domesticated animal, comprising applying to a surface of the host the following dihydronepetalactone compound: 1S,9S,5R,6R-5,9-dimethyl-3-oxabicyclo[4.3.0]nonan-2-one

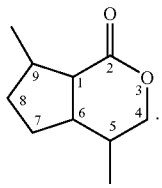

2. The method of claim 1 wherein the host is a host for a biting fly.

3. The method of claim 1 wherein the biting flies comprise one or more members of the group consisting of black flies, green head flies and stable flies.

4. The method of claim 1 wherein the host is a host for a chigger.

5. The method of claim 1 wherein the host is a host for a flea.

6. The method of claim 1 wherein the host is a host for a mosquito.

7. The method of claim 1 which comprises applying the dihydronepetalactone to skin, fur or feathers of the host.

8. The method of claim 1 wherein the host is a host for lice.

9. The method of claim 1 wherein the host is a host for one or more insects in the group consisting of biting flies, chiggers, fleas, mosquitoes and lice.

10. The method of claim 1 wherein the dihydronepetalactone is encapsulated in a protein.

11. The method of claim 1 wherein the dihydronepetalactone is encased with a polymer.

12. The method of claim 1 which comprises applying to the host a composition that comprises the dihydronepetalactone in an amount of at least about 0.001% by weight of the total weight of the composition.

13. The method of claim 1 which comprises applying to the host a composition that comprises the dihydronepetalactone in an amount of from about 0.001% to about 80% by weight of the total weight of the composition.

14. The method of claim 1 which comprises applying to the host a composition that comprises the dihydronepetalactone in an amount of from about 0.01% to about 50% by weight of the total weight of the composition.

15. The method of claim 12 wherein the composition comprises a carrier selected from the group consisting of silicone, petrolatum, lanolin, liquid hydrocarbons, agricultural spray oils, paraffin oil, tall oils, liquid terpene hydrocarbons and terpene alcohols, aliphatic and aromatic alcohols, esters, aldehydes, ketones, mineral oil, higher alcohols, finely divided organic and inorganic solid materials.

16. The method of claim 12 wherein the composition comprises an aerosol composition adapted to disperse the dihydronepetalactone into the atmosphere by means of a compressed gas.

17. The method of claim 12 wherein the composition comprises a polymeric controlled release system.

18. The method of claim 12 wherein the composition is in the form of a cologne, a lotion, a spray, a cream, a gel, an ointment, a bath or shower gel, a foam product, makeup, a deodorant, shampoo, a hair lacquer or rinse or a personal soap.

19. The method of claim 12 wherein the composition comprises one or both of an adjuvant and an insect repellent compound that is not a dihydronepetalactone.

20. The method of claim 19 wherein the adjuvant is selected from the group consisting of thickeners, buffering agents, chelating agents, preservatives, fragrances, antioxidants, gelling agents, stabilizers, surfactants, emollients, coloring agents, aloe vera, waxes, synergists and therapeutically or cosmetically active ingredients.

21. The method of claim 19 wherein the non-dihydronepetalactone insect repellent is selected from the group consisting of: benzil, benzyl benzoate, 2,3,4,5-bis(butyl-2-ene) tetrahydrofurfural, butoxypolypropylene glycol, N-butylacetanilide, normal-butyl-6,6-dimethyl-5,6-dihydro-1,4-pyrone-2-carboxylate, dibutyl adipate, dibutyl phthalate, di-normal-butyl succinate, N,N-diethyl-meta-toluamide, dimethyl carbate (endo,endo)-dimethyl bicyclo[2.2.1]hept-5-ene-2,3-dicarboxylate), dimethyl phthalate, 2-ethyl-2-butyl-1,3-propanediol, 2-ethyl-1,3-hexanediol, di-normal-propyl isocinchomeronate, 2-phenylcyclohexanol, p-methane-3,8-diol, 1-piperidinecarboxylic acid 2-(2-hydroxymethyl) 1-methylpropylester and normal-propyl N,N-diethylsuccinamate.

22. The method of claim 19 wherein the non-dihydronepetalactone insect repellent is selected from the group consisting of almond bitter oil, anise oil, basil oil, bay oil, caraway oil, cardamom oil, cedar oil, celery oil, chamomile oil, cinnamon oil, citronella oil, clove oil, coriander oil, cumin oil, dill oil, eucalyptus oil, fennel oil, ginger oil, grapefruit oil, lemon oil, lime oil, mint oil, parsley oil, peppermint oil, pepper oil, rose oil, spearmint oil (menthol), sweet orange oil, thyme oil, turmeric oil, and oil of wintergreen.

23. The method of claim 19 wherein the non-dihydronepetalactone insect repellent is selected from the group consisting of citronellal, methyl salicylate, ethyl salicylate, propyl salicylate, citronellol, safrole, and limonene.

24. The method of claim 12 wherein the composition comprises a carrier selected from the group consisting of oils produced by the distillation of coal and the distillation of petrochemical stocks.

25. The method of claim 12 wherein the composition comprises a carrier selected from the group consisting of synthetic arid natural clay, bentonite, attapulgite, fuller's earth, diatomaceous earth, kaolin, mica, talc, finely divided quartz, silica aerogels, precipitated silicas, fumed silicas, cellulose, sawdust, synthetic organic polymers, waxy solids, gels and lanolin.

26. The method of claim 15 wherein the carrier further comprises an emulsifying agent.

27. The method of claim 1 wherein the host is a human.

28. The method of claim 1 wherein the host is a dog.

29. The method of claim 1 wherein the host is poultry.

30. The method of claim 1 wherein the host is a cow.

* * * * *